United States Patent [19]

Lesher et al.

[11] 4,376,775

[45] * Mar. 15, 1983

[54] N-[4-(4-PYRIDINYL)PHENYL]UREAS AND THEIR CARDIOTONIC USE

[75] Inventors: George Y. Lesher, Schodack; Donald F. Page, East Greenbush, both of N.Y.

[73] Assignee: Sterling Drug Inc., New York, N.Y.

[*] Notice: The portion of the term of this patent subsequent to Mar. 2, 1999, has been disclaimed.

[21] Appl. No.: 285,379

[22] Filed: Jul. 20, 1981

Related U.S. Application Data

[63] Continuation-in-part of Ser. No. 152,991, May 27, 1980, Pat. No. 4,317,827.

[51] Int. Cl.$^3$ .................... C07D 213/54; A61K 31/44
[52] U.S. Cl. .................................... 424/263; 546/300; 546/332
[58] Field of Search ................. 546/300, 332; 424/263

[56] References Cited

U.S. PATENT DOCUMENTS

| | | | |
|---|---|---|---|
| 3,753,993 | 8/1973 | Lesher et al. | 546/156 |
| 3,907,808 | 9/1975 | Lesher et al. | 546/156 |
| 4,118,557 | 10/1978 | Lesher | 542/420 |

OTHER PUBLICATIONS

P. A. S. Smith, The Chemistry of Open–Chain Organic Nitrogen Compounds, vol. I, Benjamin Pub., p. 275, (1965).
Heilbron et al. [J. Chem. Soc. 1940, 1279].

*Primary Examiner*—Alan L. Rotman
*Attorney, Agent, or Firm*—Robert K. Bair; B. Woodrow Wyatt

[57] ABSTRACT

Disclosed and claimed are N-R-N-40 [4-(4-2-$R_2$-3-$R_3$-5-$R_5$-6-$R_6$-4-pyridinyl)phenyl]ureas (I) or pharmaceutically-acceptable acid-addition salts thereof, where R is hydrogen, methyl or ethyl, $R_2$ is hydrogen, methyl, ethyl or hydroxyl, $R_6$ hydrogen, methyl or ethyl, and $R_3$ and $R_5$ are each hydrogen or methyl, their cardiotonic use and their preparation.

12 Claims, No Drawings

N-[4-(4-PYRIDINYL)PHENYL]UREAS AND THEIR CARDIOTONIC USE

CROSS-REFERENCE TO RELATED APPLICATION

This application is a continuation-in-part of copending application Ser. No. 152,991, filed May 27, 1980 and now U.S. Pat. No. 4,317,827, issued Mar. 2, 1982.

BACKGROUND OF THE INVENTION (a) Field of the Invention

This invention relates to N-[4-(4-pyridinyl)phenyl]urea derivatives, their cardiotonic use and their preparation.

(b) Description of the Prior Art

Heilbron et al [J. Chem. Soc. 1940, 1279] show as intermediates in the preparation of 3- and 4-pyridyldiphenyls the following compounds: β-3-aminophenylpyridine, β-4-aminophenylpyridine and γ-4-aminophenylpyridine and the N-acetyl derivatives of each, including the hydrochloride salt of β-4-acetaminodophenylpyridine; these three aminophenylpyridines currently are named 3-(3-pyridinyl)benzeneamine 4-(3-pyridinyl)benzeneamine and 4-(4-pyridinyl)benzeneamine, respectively.

Lesher and Carabateas [U.S. Pat. Nos. 3,753,993 (Aug. 21, 1973) and 3,907,808 (Sept. 23, 1975)] show as intermediates for making quinoline antibacterial agents various 3-(substituted-pyridinyl)benzeneamines where pyridinyl is substituted, inter alia, by lower-alkyl, hydroxyl, etc., illustrated by, 3-(2-methyl-4-pyridinyl)benzeneamine, 3-(2-hydroxy-6-methyl-4-pyridinyl)benzeneamine, 3-(2,6-dimethyl-4-pyridinyl)benzeneamine, 3-(2,6-diethyl-4-pyridinyl)benzeneamine, 3-(2,5-dimethyl-4-pyridinyl)benzeneamine, 3-(3-methyl-4-pyridinyl)benzeneamine, 3-(2-ethyl-4-pyridinyl)benzeneamine, and 3-(2,3-dimethyl-4-pyridinyl)benzeneamine.

Lesher [U.S. Pat. No. 4,118,557, issued Oct. 3, 1978] shows N-(lower-alkanoyl)derivatives of various 3-(pyridinyl)benzeneamines, as illustrated as follows: N-acetyl, N-formyl, N-propanoyl, N-butanoyl and N-hexanoyl derivatives of 3-(4-pyridinyl)benzeneamine, and, the N-acetyl derivatives of 3-(2-methyl-4-pyridinyl)benzeneamine, 3-(3-pyridinyl)benzeneamine, 3-(2,6-dimethyl-4-pyridinyl)benzeneamine and 3-(2-ethyl-4-pyridinyl)benzeneamine.

SUMMARY OF THE INVENTION

A composition aspect of the invention relates to a cardiotonic composition for increasing cardiac contractility in a patient, said composition comprising a pharmaceutically-acceptable carrier and, as the active component thereof, a cardiotonic N-R-N'-[4-(4-pyridinyl)phenyl]urea or pharmaceutically-acceptable acid-addition salt thereof, where R is hydrogen, methyl or ethyl.

In a method aspect, the invention relates to a method for increasing cardiac contractility in a patient requiring such treatment which comprises administering a medicament comprising a pharmaceutically-acceptable carrier and, as the active component thereof, a cardiotonic N-R-N'-[4-(4-pyridinyl)phenyl]urea or pharmaceutically-acceptable acid-addition salt thereof, where R is defined as above.

In a composition of matter aspect, the invention relates to a N-R-N'-[4-(4-pyridinyl)phenyl]urea, or pharmaceutically-acceptable acid-addition salt thereof where R is defined as above.

In a process aspect, the invention resides in the process of producing N-R-N'-[4-(4-pyridinyl)phenyl]urea which comprises reacting the corresponding 4-(4-pyridinyl)benzeneamine with an alkali cyanate to produce said urea where R is hydrogen or with methyl or ethyl isocyanate to produce said urea where R is methyl or ethyl respectively.

DETAILED DESCRIPTION INCLUSIVE OF PREFERRED EMBODIMENTS

A composition aspect of the invention resides in a cardiotonic composition for increasing cardiac contractility, said composition comprising a pharmaceutically-acceptable inert carrier and, as the active component thereof, a cardiotonically-effective amount of N-R-N'-[4-(2-$R_2$-3-$R_3$-5-$R_5$-6-$R_6$-4-pyridinyl)phenyl]urea having formula I

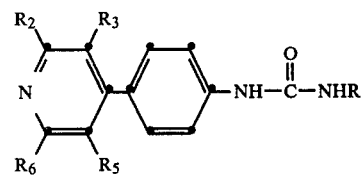

where R is hydrogen, methyl or ethyl, $R_2$ is hydrogen, methyl, ethyl or hydroxyl, $R_6$ is hydrogen, methyl or ethyl, $R_3$ and $R_5$ are each hydrogen or methyl, or pharmaceutically-acceptable acid-addition salt thereof. Preferred embodiments are those compositions where the active component is defined as above having R as hydrogen or methyl, $R_2$ as hydrogen, methyl, ethyl or hydroxyl, and, $R_3$, $R_5$ and $R_6$ are each hydrogen or methyl, or pharmaceutically-acceptable acid-addition salt thereof.

The method aspect of the invention resides in the method for increasing cardiac contractility in a patient requiring such treatment which comprises administering orally or parenterally in a solid or liquid dosage form to such patient a cardiotonically-effective amount of N-R-N'-[4-(2-$R_2$-3-$R_3$-5-$R_5$-6 $R_6$-4-pyridinyl)phenyl]urea having formula I where R, $R_2$, $R_3$, $R_5$ and $R_6$ are defined as hereinabove for the cardiotonic composition, or pharmaceutically-acceptable acid-addition salt thereof. Preferred embodiments of this aspect of the invention uses said cardiotonic where R is hydrogen or methyl, $R_2$ is hydrogen, methyl, ethyl or hydroxyl, and, $R_3$, $R_5$ and $R_6$ are each hydrogen or methyl, or pharmaceutically-acceptable acid-addition salt thereof.

In a composition of matter aspect, the invention resides in N-R-N'-[4-(2-$R_2$-3-$R_3$-5-$R_5$-6-$R_6$-4-pyridinyl)phenyl]urea having the formula I given above, where R is hydrogen, methyl or ethyl, $R_2$ is hydrogen, methyl, ethyl or hydroxyl, $R_6$ is hydrogen, methyl or ethyl, and, $R_3$ and $R_5$ are each hydrogen or methyl, or pharmaceutically-acceptable acid-addition salt thereof. Preferred embodiments of this aspect of the invention are the compounds where R is hydrogen or methyl, $R_2$ is hydrogen, methyl, ethyl or hydroxyl, and, $R_3$, $R_5$ and $R_6$ are each hydrogen or methyl, or pharmaceutically-acceptable acid-addition salt thereof.

The invention in a process aspect resides in the process of reacting 4-(2-$R_2$-3-$R_3$-5-$R_5$-6 $R_6$-4-pyridinyl)benzeneamine with an alkali cyanate to produce said urea of formula I where R is hydrogen or with methyl or ethyl isocyanate to produce said urea of formula I where R is methyl or ethyl, where $R_2$, $R_3$, $R_5$ and $R_6$ have the meanings given above for formula I.

The compounds of formula I are useful both in the free base form and in the form of acid-addition salts, and, both forms are within the purview of the invention. The acid-addition salts are simply a more convenient form for use. In practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base, the hydrochloride or the lactate. However, other appropriate pharmaceutically-acceptable salts within the scope of the invention are those derived from mineral acids such as hydrobromic acid, sulfuric acid, phosphoric acid and sulfamic acid; and organic acid such as acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, tartrate, methanesulfonate, ethanesulfonate, benzenesulfonate, p-toluenesulfonate, cyclohexylsulfamate and quinate respectively.

The acid-addition salts of the compounds of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said compounds of formula I are preferred, all acid-addition salts are within the scope of our invention. All acid-addition salts are useful as sources of the free base form even if the particular salt per se is desired only as an intermediate product, as for example when the salt is formed only for purposes of purification or identification, or when it is used as an intermediate in preparing a pharmaceutically-acceptable salt by ion exchange procedures.

The molecular structures of the novel compounds of formula I were assigned on the basis of evidence provided by infrared, nuclear magnetic resonance and mass spectra, and by the correspondence of calculated and found values for the elemental analysis.

The manner of making and using the instant invention will now be generally described so as to enable a person skilled in the art of pharmaceutical chemistry to make and use the same, as follows.

The reaction of 4-(2-$R_2$-3-$R_3$-5-$R_5$-6-$R_6$-4-pyridinyl)-benzeneamine with an alkali cyanate, preferably sodium or potassium cyanate, to produce the compound of formula I where R is hydrogen is carried out by heating the reactants at about 40° C. to 100° C., preferably at about 50° C. to 65° C. in suitable solvent, e.g., aqueous acetic acid, aqueous hydrochloric acid or aqueous sulfuric acid.

The reaction of 4-(2-$R_2$-3-$R_3$-5-$R_5$-6-$R_6$-4-pyridinyl)-benzeneamine with methyl or ethyl isocyanate to produce the compound of formula I where R is methyl or ethyl is carried out by heating the reactants at about 40° C. to 100° C., preferably at about 50° C. to 65° C. in an aprotic solvent, e.g., preferably in refluxing chloroform. Other suitable solvents include ethylene dichloride, methylene dichloride, pyridine, dimethylformamide, tetrafuran and the like. The reaction is run in the absence or presence of a catalyst, e.g., N,N-dimethyl-4-pyridineamine.

The intermediate 4-(2-$R_2$-3-$R_3$-5 $R_5$-6-$R_6$-4-pyridinyl)benzeneamines are generally known and are prepared by conventional means.

The following examples will further illustrate the invention without, however, limiting it thereto.

EXAMPLE 1

N-[4-(4-Pyridinyl)phenyl]urea—A 39.2 g. portion of 4-(4-pyridinyl)benzeneamine was dissolved in 150 ml. of warm acetic acid and 230 ml. of water was added. The solution was stirred and warmed to 55° C. on a steam bath and then a warm solution containing 74.1 g. of potassium cyanate in 460 ml. of water was added dropwise over a period of 1 hour using a dropping funnel with a long stem which dipped well below the surface of the reaction mixture. The reaction temperature was maintained at 55°-60° C. throughout the addition. A yellow solid began to form after about ⅓ of the potassium cyanate had been added. The reaction mixture was allowed to cool with continued stirring for about 30 minutes and then was allowed to stand for 2 hours. To the stirred solution was added concentrated ammonium hydroxide (about 60 ml.) to a pH of 8. The mixture was cooled well in an ice bath and the separated solid was collected, washed well with fresh water and sucked as dry as possible. The damp solid was recrystallized from 400 ml. of dimethylformamide, using decolorizing charcoal, and the recrystallized material was collected, washed with ethanol and dried in a vacuum oven at 60° C. to produce 19.3 g. of N -[4-(4-pyridinyl)phenyl]urea, m.p. 245°–247° C.

Acid-addition salts of N-[4-(4-pyridinyl)phenyl]urea are conveniently prepared by adding to a mixture of 2 g. of N-[4-(4-pyridinyl)phenyl]urea in about 40 ml. of aqueous methanol the appropriate acid, e.g., methanesulfonic acid, concentrated sulfuric acid, concentrated phosphoric acid, to a pH of about 2 to 3, chilling the mixture after partical evaporation and collecting the precipitated salt, e.g., dimethanesulfonate, sulfate, phosphate, respectively. Also, the acid-addition salt is conveniently prepared in aqueous solution by adding to water with stirring molar equivalent quantitites each of N-[4-(4-pyridinyl)phenyl]urea and the appropriate acid, e.g., lactic acid or hydrochloric acid, to prepare respectively the monolactate or monohydrochloride salt in aqueous solution.

EXAMPLE 2

N-Methyl-N'-[4-(4-pyridinyl)phenyl]urea—To 10.52 g. of 4-(4-pyridinyl)benzeneamine suspended in 400 ml. of chloroform was added with stirring 0.76 g. of N,N-dimethyl-4-pyridineamine and 5.5 ml. of methyl isocyanate. The resulting reaction mixture was stirred under reflux for sixteen hours. The reaction mixture was filtered to collect the suspended solid and the filtrate was concentrated in vacuo to yield more solid product plus an oily material. The collected solid was recrystallized from 550 ml. of acetonitrile and dried at 90° C. in vacuo to yield 6.58 g. of N-methyl-N'-[4-(4-pyridinyl)phenyl]urea, m.p. 233°–234° C. Another 3.22 g. of this product, m.p. 233°–234° C., was obtained by recrystallizing from methanol the above-noted material obtained by concentration of the reaction filtrate.

Acid-addition salts of N-methyl-N'-[4-(4-pyridinyl)phenyl]urea are conveniently prepared by adding to a mixture of 2 g. of N-methyl-N'-[4-(4-pyridinyl)phenyl]urea in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-methyl-N'-[4-(4-pyridinyl)phenyl]urea and the appropriate acid, e.g., lactic acid or hydrochloric acid, to prepare respectively the monolactate or monohydrochloride salt in aqueous solution.

EXAMPLE 3

N-Ethyl-N'-[4-(4-pyridinyl)phenyl]urea, m.p. 200°–203° C., 11.7 g., was obtained following the procedure described in Example 2 using 10 g. of 4-(4-pyridinyl)benzeneamine, 400 ml. of chloroform, 0.72 g. of N,N-dimethyl-4-pyridineamine, 7.1 ml. of 98% ethyl isocyanate and a refluxing period of twenty-four hours, followed by addition of another 7.1 ml. portion of 98% ethyl isocyanate and a second refluxing period of eight hours, filtering the reaction mixture through diatomaceous earth, concentrating the filtrate in vacuo to dryness, recrystallizing the residue from 250 ml. of acetonitrile and drying the product at 90° C. in vacuo.

Following the procedure described in Example 1 but using in place of 4-(4-pyridinyl)benzeneamine a molar equivalent quantity of the appropriate 4-(2-$R_2$-3-$R_3$-5-$R_5$-6-$R_6$-4-pyridinyl)benzeneamine, it is contemplated that the following corresponding N-[4-(2-$R_2$-3-$R_3$-5-$R_5$-6-$R_6$-4-pyridinyl)phenyl]ureas of Examples 4–8 can be obtained.

4. N-[4-(2-methyl-4-pyridinyl)phenyl]urea using 4-(2-methyl-4-pyridinyl)benzeneamine.

5. N-[4-(2-ethyl-4-pyridinyl)phenyl]urea using 4-(2-ethyl-4-pyridinyl)benzeneamine.

6. N-[4-(2-hydroxy-4-pyridinyl)phenyl]urea using 4-(2-hydroxy-4-pyridinyl)benzeneamine.

7. N-[4-(2,6-dimethyl-4-pyridinyl)phenyl]urea using 4-(2,6-dimethyl-4-pyridinyl)benzeneamine.

8. N-[4-2,3,5 trimethyl-4-pyridinyl)phenyl]urea using 4-(2,3,5-trimethyl-4-pyridinyl)benzeneamine.

Following the procedure described in Example 2 but using in place of 4-(4-pyridinyl)benzeneamine and methyl isocyanate respective molar equivalent quantities of the appropriate 4-(2-$R_2$-3-$R_3$-5 $R_5$-6 $R_6$-4-pyridinyl)benzeneamine and methyl or ethyl isocyanate, it is contemplated that the following corresponding N-(methyl or ethyl)-N'-[4-(2-$R_2$-3-$R_3$-5-$R_5$-6-$R_6$-4-pyridinyl)phenyl]ureas of Examples 9–13 can be obtained.

9. N-Methyl-N'-[4-(2-methyl-4-pyridinyl)phenyl]urea using 4-(2-methyl-4-pyridinyl)benzeneamine and methyl isocyanate.

10. N-Ethyl-N'-[4-(2-ethyl-4-pyridinyl)phenyl]urea using 4-(2-ethyl-4-pyridinyl)benzeneamine and ethyl isocyanate.

11. N'-[4-(2-hydroxy-4-pyridinyl)phenyl]-N-methylurea using 4-(2-hydroxy-4-pyridinyl)benzeneamine and methyl isocyanate.

12. N'-[4-(2,6-dimethyl-4-pyridinyl)phenyl]-N-methylurea using 4-(2,6-dimethyl-4-pyridinyl)benzenediamine and methyl isocyanate.

13. N-Methyl-N'-[4-(2,3,5-trimethyl-4-pyridinyl)phenyl]urea using 4-(2,3,5-trimethyl-4-pyridinyl)benzeneamine and methyl isocyanate.

The usefulness of the compounds of formula I or salts thereof as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I or pharmaceutically-acceptable acid-addition salts thereof at doses of 30 and/or 100 μg/ml., were found to cause significant increases, that is, greater than 25% (cat) or 30% (g. pig) in papillary muscle force and significant increases, that is, greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. The compounds of the invention (formula I) have varying degrees of cardiotonic activity. For example, the preferred embodiments of Examples 1 and 2 were found to cause respectively cat and guinea pig papillary muscle force and right atrial force increases of 58% and 26% for Example 1 (cat test) and 49% and 92% for Example 2 (g. pig test) at a dose level of 30 μg/ml., and the same respective increases of 154% and 67% for Example 1 (cat test) and 143% and 220% for Example 2 (g. pig test) at a dose level of 100 μg/ml. The embodiment of Example 3 was found to cause guinea pig papillary muscle force and right atrial force increases of 35% and 62%, respectively, at a dose level of 30 μg/ml.

When tested by said anesthetized dog procedure, the compounds of formula I or pharmaceutically-acceptable acid-addition salts thereof at doses of 1.0, 3.0 and/or 10 mg./kg. administered intravenously were found to cause significant increases, that is, 25% or greater, in cardiac contractile force or cardiac contractility with lower changes in heart rate and blood pressure. For example, when tested in three dogs at said dose levels by this procedure, the embodiment of Example 1 was found to cause average increases of 62% and 139% in contractile force at respective doses of 3 and 10 mg/kg. Similarly, when tested in three dogs by this procedure, the embodiment of Example 2 was found to cause average percentage increases in contractile force of 37%, 84% and 131% at respective doses of 1, 3 and 10 mg./kg.

The present invention includes within its scope a cardiotonic composition for increasing cardiac contractility, said composition comprising a pharmaceutically-acceptable carrier and, as the active component thereof, the cardiotonic compound of formula I or pharmaceutically-acceptable acid-addition salt thereof. The invention also includes within its scope the method for increasing cardiac contractility in a patient requiring such treatment which comprises administering to such patient an effective amount of cardiotonic compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A cardiotonic composition for increasing cardiac contractility, said composition comprising a pharmaceutically-acceptable inert carrier and, as the active component thereof, a cardiotonically-effective amount of N-R-N'-[4-(2-$R_2$-3-$R_3$-5-$R_5$-6-$R_6$-4-pyridinyl)phenyl]urea having the formula

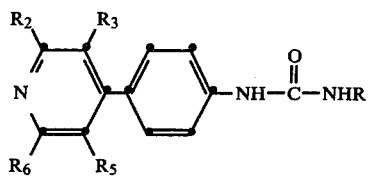

where R is hydrogen, methyl or ethyl, $R_2$ is hydrogen, methyl, ethyl or hydroxyl, $R_6$ is hydrogen, methyl or ethyl, $R_3$ and $R_5$ are each hydrogen or methyl, or pharmaceutically-acceptable acid-addition salt thereof.

2. A composition according to claim 1 where R is hydrogen or methyl, $R_2$ is hydrogen, methyl, ethyl or hydroxyl, and $R_3$, $R_5$ and $R_6$ are each hydrogen or methyl, or pharmaceutically-acceptable acid-addition salt thereof.

3. A composition according to claim 1 where the cardiotonic is N-[4-(4-pyridinyl)phenyl]urea or pharmaceutically-acceptable acid-addition salt thereof.

4. A composition according to claim 1 where the cardiotonic is N-methyl-N'-[4-(4-pyridinyl)phenyl]urea or pharmaceutically-acceptable acid-addition salt thereof.

5. The method for increasing cardiac contractility in a patient requiring such treatment which comprises administering orally or parenterally in a solid or liquid dosage form to such patient a cardiotonically-effective amount of N-R-N'-[4-2-$R_2$-3-$R_3$-5-$R_5$-6-$R_6$-4-pyridinyl)phenyl]urea having the formula

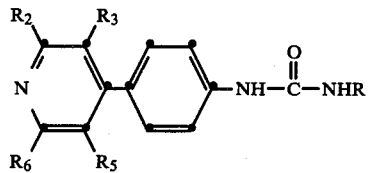

where R is hydrogen, methyl or ethyl, $R_2$ is hydrogen, methyl, ethyl or hydroxyl, $R_6$ is hydrogen, methyl or ethyl, $R_3$ and $R_5$ are each hydrogen or methyl, or pharmaceutically-acceptable acid-addition salt thereof.

6. The method according to claim 5 where R is hydrogen or methyl, $R_2$ is hydrogen, methyl, ethyl or hydroxyl, and $R_3$, $R_5$ and $R_6$ are each hydrogen or methyl, or pharmaceutically-acceptable acid-addition salt thereof.

7. The method according to claim 5 where the cardiotonic is N-[4-(4-pyridinyl)phenyl]urea or pharmaceutically-acceptable acid-addition salt thereof.

8. The method according to claim 5 where the cardiotonic is N-methyl-N'-[4-(4-pyridinyl)phenyl]urea or pharmaceutically-acceptable acid-addition salt thereof.

9. An N-R-N'-[4-(2-$R_2$-3-5 $R_5$-6-$R_6$-4-pyridinyl)phenyl]urea having the formula

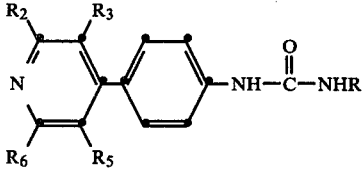

where R is hydrogen, methyl or ethyl, $R_2$ is hydrogen, methyl, ethyl or hydroxyl, $R_6$ is hydrogen, methyl or ethyl, $R_3$ and $R_5$ are each hydrogen or methyl, or pharmaceutically-acceptable acid-addition salt thereof.

10. A compound according to claim 9 where R is hydrogen or methyl, $R_2$ is hydrogen, methyl, ethyl or hydroxyl, and $R_3$, $R_5$ and $R_6$ are each hydrogen or methyl, or pharmaceutically-acceptable acid-addition salt thereof.

11. N-[4-(4-pyridinyl)phenyl]urea or pharmaceutically-acceptable acid-addition salt thereof.

12. N-methyl-N'-[4-(4-pyridinyl)phenyl]urea or pharmaceutically-acceptable acid-addition salt thereof.

* * * * *

UNITED STATES PATENT AND TRADEMARK OFFICE
CERTIFICATE OF CORRECTION

PATENT NO.   :   4,376,775
DATED        :   March 15, 1983
INVENTOR(S)  :   G.Y. Lesher et al.

It is certified that error appears in the above-identified patent and that said Letters Patent is hereby corrected as shown below:

Abstract, face page, line 1, "-N-40[4-" should read -- N'-[4- --.

Column 1, line 23, "-acetaminodo" should read -- acetamido --.

Claim 4, line 2, "-N-'-" should read -- -N'- --.

Claim 9, line 1, "-3-5" should read -- -3-$R_3$-5- --.

Signed and Sealed this

Twenty-first Day of May 1985

[SEAL]

Attest:

DONALD J. QUIGG

Attesting Officer

Acting Commissioner of Patents and Trademarks